United States Patent
Wang et al.

(10) Patent No.: US 11,317,826 B2
(45) Date of Patent: May 3, 2022

(54) APPARATUS, METHOD AND SYSTEM FOR MONITORING RESPIRATORY STATE

(71) Applicants: HEFEI BOE OPTOELECTRONICS TECHNOLOGY CO., LTD., Anhui (CN); BOE TECHNOLOGY GROUP CO., LTD., Beijing (CN)

(72) Inventors: Wenjian Wang, Beijing (CN); Jingwen An, Beijing (CN)

(73) Assignees: HEFEI BOE OPTOELECTRONICS TECHNOLOGY CO., LTD., Anhui (CN); BOE TECHNOLOGY GROUP CO., LTD., Beijing (CN)

( * ) Notice: Subject to any disclaimer, the term of this patent is extended or adjusted under 35 U.S.C. 154(b) by 235 days.

(21) Appl. No.: 16/610,746

(22) PCT Filed: Jan. 28, 2019

(86) PCT No.: PCT/CN2019/073308
§ 371 (c)(1),
(2) Date: Nov. 4, 2019

(87) PCT Pub. No.: WO2019/218723
PCT Pub. Date: Nov. 21, 2019

(65) Prior Publication Data
US 2021/0330214 A1    Oct. 28, 2021

(30) Foreign Application Priority Data
May 15, 2018    (CN) .......................... 201810462111.2

(51) Int. Cl.
*A61B 5/087* (2006.01)
*A61B 5/00* (2006.01)
*A61B 5/08* (2006.01)

(52) U.S. Cl.
CPC ............ *A61B 5/087* (2013.01); *A61B 5/0022* (2013.01); *A61B 5/0826* (2013.01);
(Continued)

(58) Field of Classification Search
CPC ....... A61B 5/087; A61B 5/0826; A61B 5/097; A61B 5/0836; A61B 5/091
See application file for complete search history.

(56) References Cited

U.S. PATENT DOCUMENTS

| | | |
|---|---|---|
| 8,679,012 B1 | 3/2014 | Kayyali |
| 2014/0194703 A1 | 7/2014 | Wondka et al. |
| 2021/0205559 A1* | 7/2021 | Raman .................... A61B 5/087 |

FOREIGN PATENT DOCUMENTS

| | | |
|---|---|---|
| CN | 1095578 A | 11/1994 |
| CN | 200994777 Y | 12/2007 |

(Continued)

OTHER PUBLICATIONS

Gouma, et al., A selective nanosensor device for exhaled breath analysis, Sep. 6, 2011, Journal of Breath Research, 5, p. 1-6 (Year: 2011).*

(Continued)

*Primary Examiner* — Daniel L Cerioni
*Assistant Examiner* — Raymond P Dulman
(74) *Attorney, Agent, or Firm* — Myers Bigel, P.A.

(57) ABSTRACT

This disclosure provides an apparatus, method and system for monitoring respiratory state. The apparatus includes an airflow sensor configured to monitor an exhalation flow of a subject, and a controller configured to determine whether the subject is experiencing an apnea according to the monitored exhalation flow and issue an alarm signal in response to determining that the subject is experiencing an apnea. Thereby, health problems caused by apnea are avoided.

15 Claims, 4 Drawing Sheets

(52) U.S. Cl.
CPC ............ *A61B 5/7405* (2013.01); *A61B 5/746* (2013.01); *A61B 5/7455* (2013.01)

(56) References Cited

FOREIGN PATENT DOCUMENTS

| | | | |
|---|---|---|---|
| CN | 105025790 | A | 11/2015 |
| CN | 106310483 | A | 1/2017 |
| CN | 108814606 | A | 11/2018 |

OTHER PUBLICATIONS

First Office Action and English language translation, CN Application No. 201810462111.2, dated May 5, 2019, 17 pp.
Second Office Action and English language translation, CN Application No. 201810462111.2, dated Oct. 15, 2019, 22 pp.
Rejection on Decision and English language translation, CN Application No. 201810462111.2, dated Jan. 7, 2020, 19 pp.
Kitagawa et al., "Basis and design of adsorption" with English language translation, Chemical Industry Press, First edition, Apr. 1983, 8 pp.
Wang et al., "Adsorption performance of CO2 on spherical macrporous resin loaded polyethylenimine" with English language Abstract, Scientia Sinica Chimica, vol. 42, No. 3, Mar. 15, 2012, pp. 306-312.

\* cited by examiner

APPARATUS, METHOD AND SYSTEM FOR MONITORING RESPIRATORY STATE

CROSS REFERENCE TO RELATED APPLICATIONS

The present application is a 35 U.S.C. 371 national stage application of PCT International Application No. PCT/CN2019/073308, filed on Jan. 28, 2019, which claims the priority of Chinese patent application No. 201810462111.2 filed on May 15, 2018, the entire disclosures of which are incorporated herein by reference as part of the present application.

TECHNICAL FIELD

This disclosure relates to the technical field of medical monitoring, and in particular to an apparatus, a method and a system for monitoring respiratory state.

BACKGROUND ART

In daily life, snoring is very common, and a few of us take it seriously. However, research reports show that snoring is a threat to health because it may repeatedly interrupt breathing during sleep, which may cause severe hypoxia in the brain and in the blood and thus form hypoxemia. This will in turn induce high blood pressure, arrhythmia, myocardial infarction, angina and other diseases. What's even worse, a long-time apnea may lead to sudden death.

Therefore, to detect apnea in time is an urgent problem to be solved.

SUMMARY

According to an aspect of the embodiments of this disclosure, an apparatus for monitoring respiratory state is provided. The apparatus comprises an airflow sensor and a controller. The airflow sensor is configured to monitor an exhalation flow of a subject. The controller is configured to determine whether the subject is experiencing an apnea according to the monitored exhalation flow and issue an alarm signal in response to determining that the subject is experiencing an apnea.

In some embodiments, the airflow sensor is an air flow amount sensor. The controller is configured to: compare an air flow amount of the exhalation flow monitored by the air flow amount sensor with a preset flow mount threshold; determine that the subject is experiencing an apnea in response to the air flow amount of the exhalation flow being lower than the flow mount threshold; and issue the alarm signal in response to determining that the subject is experiencing an apnea and a duration of the apnea exceeding a preset duration threshold.

In some embodiments, the apparatus further comprises a wireless network module. The controller is configured to issue the alarm signal by sending the alarm signal to an alarm device via the wireless network module.

In some embodiments, the alarm device comprises a terminal device associated with the subject. The terminal device wakes the subject or reports an emergency of the subject haptically or audibly.

In some embodiments, the alarm device comprises a vibrator arranged in an appliance in contact with the subject. The alarm signal carries a vibration instruction such that the vibrator vibrates in accordance with the vibration instruction to wake the subject.

In some embodiments, the apparatus further comprises a trigger connected with the controller and the wireless network module respectively and configured to trigger initiation of the wireless network module. The trigger comprises a charge generator and a charge collector. The charge generator is coupled to the controller, and configured to be controlled to switch on in response to the controller determining that the subject is experiencing an apnea, and generate charges in an ON state. The charge collector is connected with the charge generator and the wireless network module respectively, and configured to collect the charges generated by the charge generator, and, in response to an amount of the collected charges reaching a preset charge amount, trigger initiation of the wireless network module such that the wireless network module sends the alarm signal by transmitting outward the signal.

In some embodiments, the airflow sensor is filled with a material capable of adsorbing carbon dioxide. The carbon dioxide in the exhalation flow is adsorbed by the material. The controller is configured to obtain a weight of the material with adsorbed carbon dioxide and control the charge generator to be in an OFF state in response to the obtained weight exceeding a preset weight threshold.

In some embodiments, the apparatus further comprises a heater. The controller is further configured to control the heater to switch on upon detection of the exhalation flow by the airflow sensor so as to heat the material with adsorbed carbon dioxide to release the adsorbed carbon dioxide.

According to another aspect of the embodiments of this disclosure, a method for monitoring respiratory state is provided. The method comprises: monitoring an exhalation flow of a subject; determining whether the subject is experiencing an apnea according to the monitored exhalation flow; and issuing an alarm signal in response to determining that the subject is experiencing an apnea.

In some embodiments, determining whether the subject is experiencing an apnea comprises: comparing an air flow amount of the monitored exhalation flow with a preset flow mount threshold; determining that the subject is experiencing an apnea in response to the air flow amount of the exhalation flow being lower than the flow mount threshold; and issuing the alarm signal in response to determining that the subject is experiencing an apnea and a duration of the apnea exceeding a preset duration threshold.

In some embodiments, issuing the alarm signal comprises: sending the alarm signal to an alarm device wirelessly.

In some embodiments, the alarm device comprises a terminal device associated with the subject, and the terminal device wakes the subject or reports an emergency of the subject haptically or audibly.

In some embodiments, the alarm device comprises a vibrator arranged in an appliance in contact with the subject and the alarm signal carries a vibration instruction such that the vibrator vibrates in accordance with the vibration instruction to wake the subject.

In some embodiments, the method further comprises: controlling a charge generator to switch on to generate charge in response to determining that the subject is experiencing an apnea, collecting by a charge collector the charges generated by the charge generator, and triggering to send the alarm signal wirelessly in response to an amount of the charges collected by the charge collector reaching a preset charge amount.

In some embodiments, the method further comprises: adsorbing carbon dioxide in the exhalation flow with a material capable of adsorbing carbon dioxide; obtaining a weight of the material with adsorbed carbon dioxide; and comparing the obtained weight with a preset weight threshold, and controlling the charge generator to be in an OFF state in response to the weight exceeding the weight threshold.

In some embodiments, the method further comprises: upon detection of the exhalation flow, heating the material with adsorbed carbon dioxide to release the adsorbed carbon dioxide.

According to yet another aspect of the embodiments of this disclosure, a further apparatus for monitoring respiratory state is provided. The apparatus comprises an airflow sensor and a controller. The controller comprises a charge generator coupled to the airflow sensor and a charge collector connected with the charge generator. The apparatus further comprises an alert device connected with the charge collector. The airflow sensor is configured to monitor an exhalation flow of a subject. The charge generator is configured to generate charges in an ON state. The charge generator is configured to be in an OFF state in response to the monitored exhalation flow indicating that the subject breathes normally and in the ON state in response to the monitored exhalation flow indicating that the subject pauses breathing. The charge generator generates charges in the ON state. The charge collector is configured to collect the charges generated by the charge generator when the charge generator is in the ON state. The controller is configured to determine that the subject is experiencing an apnea in response to an amount of the charges collected by the charge collector reaching a preset charge amount. The alert device is configured to issue an alarm signal in response to the amount of the charges collected by the charge collector reaching the preset charge amount.

In some embodiments, the alert device is configured to issuing the alarm signal by sending the alarm signal to an alarm device.

In some embodiments, the airflow sensor comprises a gas sensitive resistor sensitive to carbon dioxide. The airflow sensor is configured to: detect an input voltage of the gas sensitive resistor, control the charge generator to be in the ON state if the input voltage does not exceed a preset voltage value, and control the charge generator to be in an OFF state if the input voltage exceeds the preset voltage value.

In some embodiments, the airflow sensor is connected with a first switch on the charge generator. The first switch switches off the charge generator in response to the input voltage exceeding the preset voltage value.

In some embodiments, the alert device further comprises a wireless network module connected with the charge collector. The wireless network module is connected with the charge collector via a second switch. The second switch is closed in response to the amount of the charges collected by the charge collector reaching the preset charge amount. The wireless network module is configured to send outward the alarm signal in response to the second switch being closed.

According to a still further aspect of the embodiments of this disclosure, a storage medium having computer instructions stored thereon is provided. The computer instructions when executed by a processor implement one or more steps of the method for monitoring respiratory state according to the above embodiments.

According to a still further aspect of the embodiments of this disclosure, an electronic device is provided. The electronic device comprises one or more processors and a memory having computer instructions stored thereon. The one or more processors are configured to execute the computer instructions to implement one or more steps of the method for monitoring respiratory state according to the above embodiments.

According to a still further aspect of the embodiments of this disclosure, a system for monitoring respiratory state is provided. The system comprises the apparatus for monitoring respiratory state according to the above embodiments and an alarm device. The alarm device is configured to receive the alarm signal issued by the apparatus and wake the subject or report an emergency of the subject in response to the alarm signal.

BRIEF DESCRIPTION OF DRAWINGS

The above and/or additional aspects and advantages of this disclosure will become apparent and clear through depictions of the embodiments with reference to the drawings, wherein.

DETAILED DESCRIPTION OF EMBODIMENTS

Figure 1:
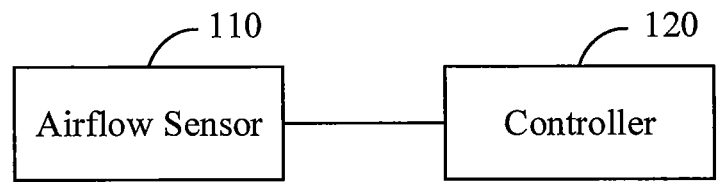
FIG. 1 is a schematic structure view of an apparatus for monitoring respiratory state provided in the embodiments of this disclosure.

The embodiments of this disclosure will be described in detail and examples of the embodiments will be shown in the drawings, wherein same or similar signs are used to indicate same or similar elements or elements having same or similar functions throughout. The embodiments described below with reference to the drawings are exemplary, and they are intended for explaining this disclosure rather than limiting this disclosure.

According to clinical diagnostic standards, sleep apnea (SA) refers to a symptom in which respiratory airflows from the mouth and the nose both stop for more than 10 seconds during sleep. With regard to the phenomenon that a long-time apnea may cause a series of health problems, an apparatus for monitoring respiratory state is provided in the embodiments of this disclosure. The apparatus comprises an airflow sensor and a controller. The controller determines whether an apnea occurs based on an exhalation flow of a subject monitored by the airflow sensor. When it is determined that an apnea occurs, an alarm signal is issued to wake the subject. Thereby, the health problems caused by a long-time apnea are avoided. Meanwhile, since the apparatus only monitors the exhalation flow of the subject, the cost of the apparatus is greatly reduced.

FIG. 1 is a schematic structure view of an apparatus for monitoring respiratory state provided in the embodiments of this disclosure. As shown in FIG. 1, the apparatus for monitoring respiratory state comprises: an airflow sensor 110 and a controller 120.

The airflow sensor 110 is configured to monitor an exhalation flow of a subject. In some embodiments, the airflow sensor 110 can be used to monitor the exhalation flow of the subject when the subject is in a sleep state or a sleep-like state (such as a coma state or other unconscious states). Exemplarily, the airflow sensor 110 may be a sensor based on a thermistor, a thermosensitive crystal, or a piezoelectric crystal. In some embodiments, the airflow sensor 110 may also be a sensor based on gas sensitive resistor.

In some embodiments, the subject may be a person having an apnea symptom or a patient whose respiratory state needs to be monitored. The airflow sensor 110 may be disposed above or worn on the face of the person, so as to monitor an airflow exhaled thereby.

The controller 120 is configured to determine whether the subject is experiencing an apnea in a current state according to the monitored exhalation flow of the subject. The controller 120 issues an alarm signal in response to determining that the subject is experiencing an apnea. In some cases, the alarm signal can be used for waking the subject. Exemplarily, it can be determined that an apnea occurs when an interruption in the airflow is detected during the exhalation of airflow by the subject. Optionally, the controller 120 may not issue an alarm signal until the duration of apnea (which for example can refer to the length of time for which the exhalation flow remains interrupted since the apnea is determined) exceeds a preset duration threshold. Optionally, the controller 120 may not issue an alarm signal until the number of apneas exceeds a preset threshold within a certain monitoring period. The duration threshold may be set according to actual needs or based on clinical experience values.

In some embodiments, the controller 120 may issue an alarm signal by instructing to send the alarm signal to an alarm device associated with the subject. An example of the alarm device comprises a terminal device. The terminal device may wake the subject by means of tactile (e.g., vibrations) or auditory (e.g., sound prompts) after receiving the alarm signal. The terminal device may be a mobile terminal such as a cellphone or a tablet computer, or a wearable device such as a smart wristband or a smart watch. In some embodiments, the terminal device may also be a traditional computer, e.g., a desktop personal computer or a laptop computer.

As an application scene, the apparatus for monitoring respiratory state according to the embodiments of this disclosure can be used in a smart home environment. This apparatus can be used to monitor whether a person is experiencing an apnea when he/she is asleep. If an apnea occurs and optionally the duration of apnea exceeds the preset duration threshold, an alarm signal may be sent to the terminal device so as to wake the person from sleep in time to resume breathing normally. In some embodiments, the terminal device may be disposed in the vicinity of the subject to be monitored (e.g., worn by the subject to be monitored). As another application scene, the apparatus for monitoring respiratory state according to the embodiments of this disclosure can be used in the medical field for monitoring a patient. In this way, when the apparatus detects that the patient is experiencing an apnea and optionally the duration of apnea exceeds a preset duration threshold, an alarm signal may be sent to a terminal device monitored by the medical staff such that the medical staff can treat the patient in time.

By issuing an alarm signal upon determination that the subject is experiencing an apnea, the apparatus for monitoring respiratory state according to the embodiments of this disclosure can avoid health problems caused by a long-time apnea. Meanwhile, since the apparatus only monitors the exhalation flow of the subject, the cost of the apparatus is greatly reduced.

Figure 2:
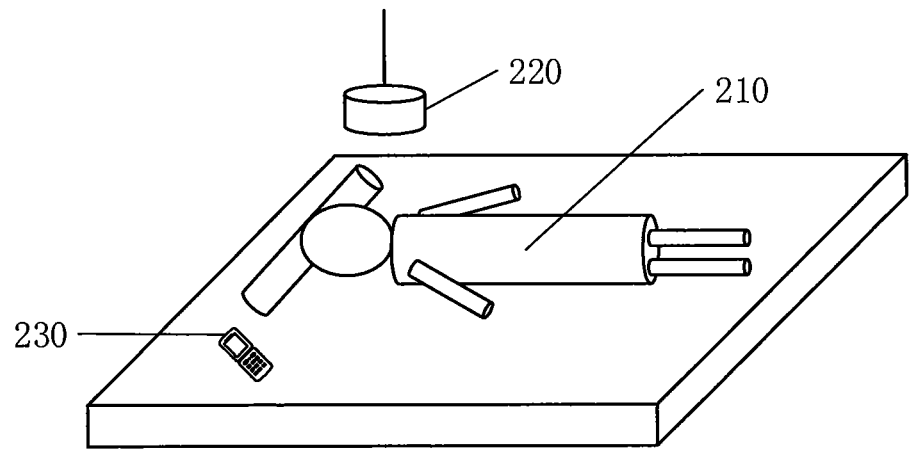
FIG. 2 is a schematic view of monitoring respiratory state according to the embodiments of this disclosure.

FIG. 2 is a schematic view showing a scene of implementing the monitoring of respiratory state according to the embodiments of this disclosure. As shown in FIG. 2, when the person 210 is in a lying state, the airflow sensor in the monitoring apparatus 220 for monitoring respiratory state can be disposed above the human face to detect the airflows exhaled by the person in this state. In order to avoid influences on the person's breathing by the airflow sensor, a distance between the airflow sensor and the face of the person 210 can be controlled within a preset distance threshold.

The controller in the monitoring apparatus 220 can determine whether the person is experiencing an apnea in the current state based on an exhalation flow monitored by the airflow sensor. Since no airflow is exhaled or little airflow is exhaled when a person is in apnea or has weak breathing, the air flow a person exhales can be used to determine whether he/she is experiencing an apnea. Exemplarily, the airflow sensor can be a air flow amount sensor. Thereby, the controller can obtain from the airflow sensor the air flow amount of the exhalation flow of the subject monitored at the moment. The controller is configured to compare the obtained air flow amount of the exhalation flow with a preset flow mount threshold. It is determined that the subject is experiencing an apnea in the current state in response to the air flow amount of the exhalation flow being lower than the flow mount threshold.

In some embodiments, in order to avoid disturbances to a user by alarms issued in case of a short-time apnea, an alarm signal is not issued immediately once the subject is detected to be experiencing an apnea in the current state, but instead it is not issued until the duration of the apnea exceeds a preset duration threshold. This can reduce disturbances to the subject and improve the accuracy of alarm. To take the sleep state as an example, medical studies indicate that people are prone to sudden death in the early morning when an apnea lasts over 120 seconds, so the duration threshold of the apnea in the sleep state can be set as 100 seconds. The controller begins timing once it is determined that the person is in apnea. When the apnea lasts over 100 seconds, the controller may send out an alarm signal to a terminal device 230 such that the terminal device 230 wakes the person in response to the alarm signal. Thereby, the health problems caused by a long-time apnea can be avoided.

Figure 3:
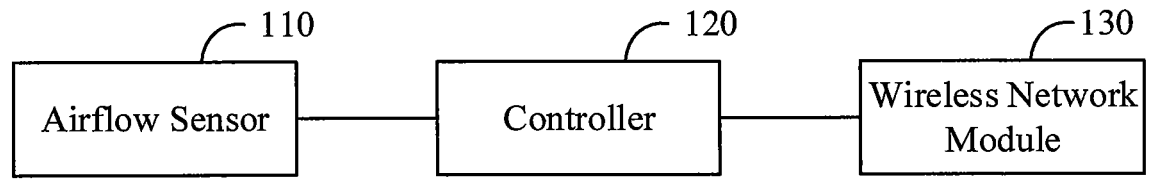
FIG. 3 is a schematic structure view of a further apparatus for monitoring respiratory state provided in the embodiments of this disclosure.

FIG. 3 is a schematic structure view of another apparatus for monitoring respiratory state provided in the embodiments of this disclosure. In addition to the airflow sensor 110 and the controller 120 similar to those in FIG. 1, the apparatus for monitoring respiratory state shown in FIG. 3 further comprises a wireless network module 130.

The wireless network module 130 is configured to establish, when the controller 120 determines that the subject is experiencing an apnea and optionally the duration of the apnea exceeds a preset duration threshold, a wireless connection with an alarm device so as to send an alarm signal to the alarm device, thereby waking the subject or issuing an alarm to report the current emergency of the subject.

In some embodiments, the wireless network module 130 may be a wireless communication module, e.g., a short-distance wireless communication module like a Blue Tooth module, a wife module and so on. When the alarm device receives the alarm signal, it may wake the subject or issue an alarm by means of vibration or sound prompts in response to the alarm signal.

As another possible implementation, when the subject, e.g., a person, is lying on a bed with a pillow, the alarm device may be an appliance in contact with the subject, such as the pillow or a quilt. For example, the pillow used by the subject may have a vibrator installed therein. In this way, when the controller 120 issues an alarm signal, it may send via the wireless network module 130 an alarm signal carrying vibration instructions to the vibrator in the pillow of the subject, such that the vibrator vibrates according to the vibration instructions in the alarm signal, thereby waking the subject.

The vibration instructions may comprise vibration-related parameters, such as information about vibration duration, vibration frequency or decibel during the vibration. For instance, the vibration instructions may be arranged in such a way: the vibration duration is 5 seconds, the vibration frequency is 3 times per second or the vibration decibel is 30 decibels. The vibrator may vibrate correspondingly in accordance with the parameters in the vibration instructions.

In some embodiments, by sending via the wireless network module an alarm signal to the vibrator in an appliance in contact with the subject, the subject can be rapidly woken, which avoids serious consequences caused by an excessively long-time apnea.

Alternatively, the apparatus for monitoring the respiratory state may also be connected with the alarm device such as a terminal device or appliance in a wired manner such that the controller can instruct to send the alarm signal to the alarm device via a wired network.

Figure 4:
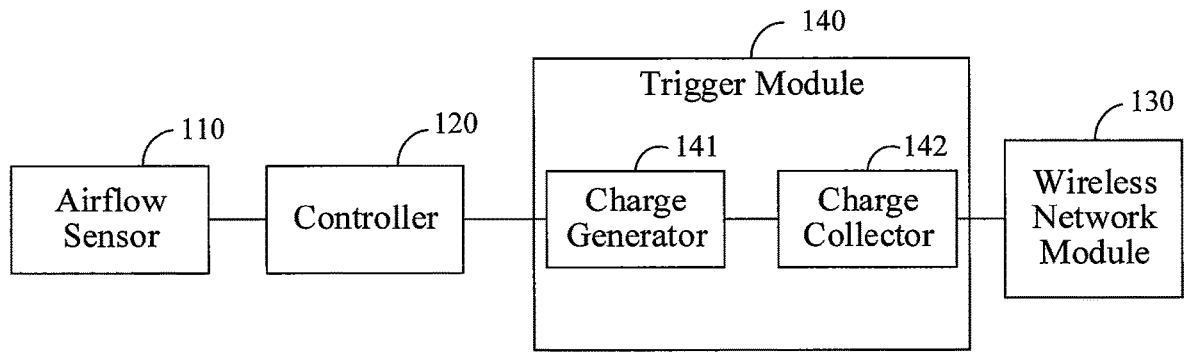
FIG. 4 is a schematic structure view of a still further apparatus for monitoring respiratory state provided in the embodiments of this disclosure.

In some embodiments, in order to improve the accuracy of sending an alarm signal, the apparatus is configured such that the wireless network module is triggered and initiated to transmit outward a signal only when a certain condition is satisfied. FIG. 4 is a schematic structure view of yet another apparatus for monitoring respiratory state provided in the embodiments of this disclosure. In addition to the airflow sensor 110, the controller 120 and the wireless network module 130 similar to those in FIG. 3, the apparatus for monitoring respiratory state shown in FIG. 4 may further comprise a trigger module 140.

The trigger module 140 may be connected with the controller 120 and the wireless network module 130 respectively and configured to initiate the wireless network module 130. In some embodiments, the trigger module 140 may comprise a charge generator 141 and a charge collector 142.

The charge generator 141 can be coupled to the controller 120 and configured to be switched on under the control of the controller 120 and generate charges in an ON state. In some embodiments, initially, the charge generator 141 is in an OFF state. The controller 120 can control the charge generator 141 to switch on when it determines that the subject is experiencing an apnea.

The charge collector 142 is connected with the charge generator 141 and the wireless network module 130 respectively, and configured to collect the charges generated by the charge generator 141. When an amount of the collected charges reaches a preset charge amount, the wireless network module 130 is triggered to initiate such that the wireless network module 130 transmits outward a signal in order to send an alarm signal. Optionally, when the wireless network module 130 is initiated, the controller 120 switches off the charge generator 141 and resets the charge collector 142 to avoid accumulation of charges in the charge collector. Additionally, the charge collector 142 may also be manually reset.

In some embodiments, the airflow sensor 110 may be filled with a material capable of adsorbing carbon dioxide (i.e., a carbon dioxide adsorbent), and the carbon dioxide in the exhalation flow is adsorbed by the material. The controller 120 can be configured to obtain a weight of the material with adsorbed carbon dioxide and determine the subject is in a normal breathing state in response to the weight exceeding a preset weight threshold, thereby controlling the charge generator 141 to keep in the OFF state.

In an exemplary scene, when the subject breathes normally, carbon dioxide in the exhalation flow is adsorbed by the carbon dioxide adsorbent with which the airflow sensor 110 is filled. Each time the subject breathes, i.e., in each respiratory (exhalation/inhalation) cycle, carbon dioxide in the exhalation flow is adsorbed by the carbon dioxide adsorbent with which the airflow sensor 110 is filled. The controller 120 can obtain the weight of the material with adsorbed carbon dioxide and compare the obtained weight with the preset weight threshold. If the weight exceeds the preset weight threshold, it means that the subject is in a normal exhalation state, so the controller 120 can control the charge generator to remain in the OFF state. In some embodiments, the controller 120 can determine an exhalation duration of the subject in accordance with a respiratory cycle of the subject, and obtain a weight of the material with adsorbed carbon dioxide after the subject completes the exhalation. In some embodiments, the controller 120 can obtain the weight of the material by means of a weight sensor for instance.

When the charge generator 141 is in the OFF state, it stops generating charges. At this point, the charge collector 142 collects no charges, and the amount of collected charges stops increasing.

It can be understood that when the subject is experiencing an apnea, no airflow is exhaled in a general exhalation duration, so the weight of the carbon dioxide adsorbent in the airflow sensor does not change. At this point, the controller 120 can control the charge generator 141 to switch on. The charge generator 141 generates charges in the ON state and the generated charges are collected by the charge collector 142. When the amount of the charges collected by the charge collector 142 reaches the preset charge amount, initiation of the wireless network module 130 is triggered such that the wireless network module 130 transmits outward a signal in order to send an alarm signal.

When the subject breathes normally, the carbon dioxide adsorbent with which the airflow sensor is filled will continuously adsorb and accumulate carbon dioxide. A possible situation may occur, in which although the subject has experienced an apnea, no alarm signal will be sent since the charge generator is still in an OFF state due to the carbon dioxide accumulated in the material with adsorbed carbon dioxide.

Figure 5:
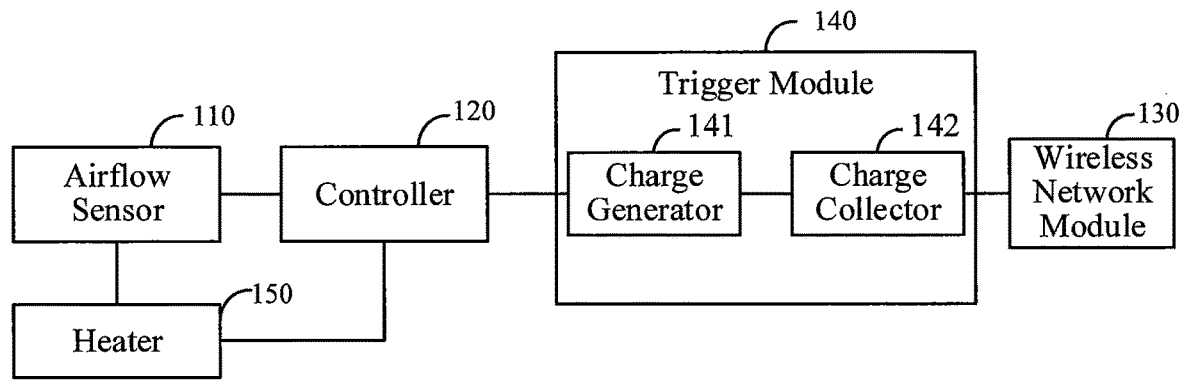
FIG. 5 is a schematic structure view of a still further apparatus for monitoring respiratory state provided in the embodiments of this disclosure.

To improve the accuracy of alarm, in some embodiments, the material with adsorbed carbon dioxide is heated every time there is an airflow exhaled. FIG. 5 is a schematic structure view of a still further apparatus for monitoring respiratory state provided in the embodiments of this disclosure. In addition to the airflow sensor 110, the controller 120, the wireless network module 130 and the trigger module 140 similar to those in FIG. 4, the apparatus for monitoring respiratory state shown in FIG. 5 may further comprise a heater 150.

Referring to FIG. 5, the heater 150 is connected with the airflow sensor 110 and configured to heat the material with adsorbed carbon dioxide in the airflow sensor to release the carbon dioxide adsorbed therein. In some embodiments, the controller 120 is configured to switch on the heater 150 for heating when the airflow sensor 110 detects an exhalation flow, i.e., it is determined that the subject is in an normal breathing state. Alternatively, the controller 120 may also switches on the heater 150 for heating periodically (e.g., every n respiratory cycles, n>=1) based on the respiratory cycle of the subject when it determines that the subject is in a normal breathing state.

Exemplarily, each time the airflow sensor 110 detects an exhalation flow, i.e., each time the subject breathes, the controller 120 controls the heater 150 to switch on once for heating the airflow sensor 110 such that the material with adsorbed carbon dioxide releases the adsorbed carbon dioxide, thereby restoring the material. Alternatively, the duration of a heating interval may also be determined based on the carbon dioxide adsorbing/releasing capability of the material. In some embodiments, the heating duration of the heater is set to be smaller than the duration of the inhalation in the respiratory cycle of the subject so as to facilitate detection of each exhalation of the subject.

Optionally, the heater may be arranged inside the airflow sensor, but it can be understood that the embodiments of this disclosure are not limited thereto. In actual application, the position of the heater may be arranged as desired.

According to the embodiments of this disclosure, after the material adsorbs carbon dioxide, the heater is switched on to heat the material with adsorbed carbon dioxide to release the carbon dioxide therefrom. This not only recycles the material, but also avoids the problem that the charge generator continuously remains in an OFF state in case of an apnea of the subject, which is caused by accumulation of carbon dioxide adsorbed by the material in the airflow sensor during normal breathing. Then, the alarm signal can be sent more accurately.

In an example, the carbon dioxide adsorbent can be calcium hydroxide. Accordingly, when the person breathes, the exhaled carbon dioxide will combine with calcium hydroxide to form calcium carbonate. Upon detection of an exhalation flow by the airflow sensor, the controller switches on the heater to heat the calcium carbonate such that the calcium carbonate decomposes under the heating to release carbon dioxide and obtain calcium hydroxide. In this way, the calcium hydroxide can be recycled.

Figure 6:
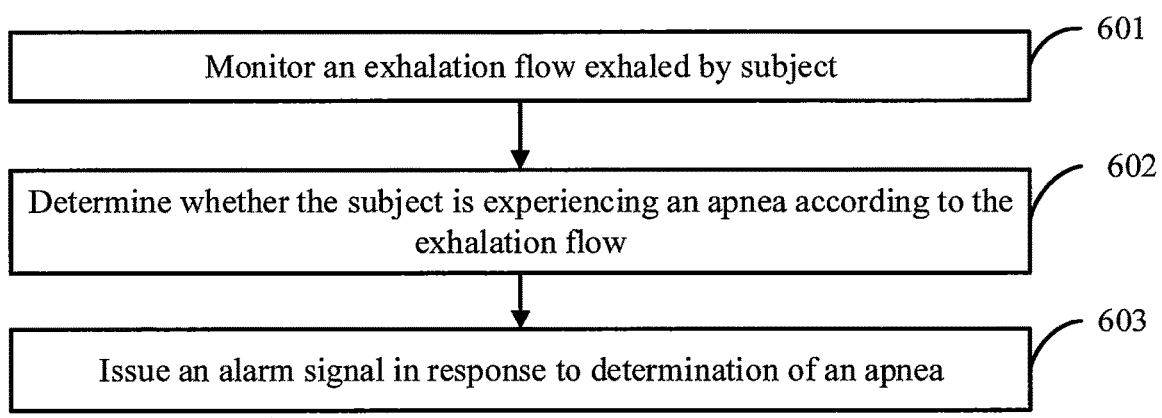
FIG. 6 is a flow chart showing a method for monitoring respiratory state provided in the embodiments of this disclosure.

FIG. 6 is a flow chart showing a method for monitoring respiratory state provided in the embodiments of this disclosure. The method for monitoring respiratory state in the embodiments of this disclosure may be executed by an apparatus for monitoring respiratory state according to the embodiments of this disclosure.

In step 601, an exhalation flow exhaled by a subject is monitored. In some embodiments, an airflow sensor in the apparatus for monitoring respiratory state can be used for monitoring an exhalation flow exhaled by the subject. For example, the airflow sensor can be used to monitor the exhalation flow of the subject when the subject is in a sleep state, a coma state or other unconscious states. In some embodiments, the airflow sensor may be worn on the face of the subject in order to collect the exhalation flow of the subject.

In step 602, whether the subject is experiencing an apnea in the current state is determined according to the exhalation flow. Since there is an airflow exhaled when a person breathes and there is no airflow exhaled when he/she pauses breathing, in some embodiments, the controller in the apparatus for monitoring respiratory state may determine whether the subject is experiencing an apnea based on the exhalation flow monitored by the airflow sensor. In some embodiments, it can be determined whether the subject is experiencing an apnea based on a air flow amount of the exhalation flow. The greater the air flow amount of the exhalation flow is, the less likely the subject is to have an apnea. Exemplarily, the air flow amount of the exhalation flow monitored by the airflow sensor can be measured and then compared with a preset flow mount threshold. It is determined that the subject is experiencing an apnea in the current state if the air flow amount of the exhalation flow is lower than the flow mount threshold. In some embodiments, by determining whether the subject is experiencing an apnea based on the air flow amount of the exhalation flow, the accuracy of the detection can be improved.

In step 603, an alarm signal is issued in response to determining that the subject is experiencing an apnea. In some embodiments, timing is started since it is determined that the subject is experiencing an apnea, and when the duration of the apnea exceeds a preset duration threshold, the alarm signal is issued to an alarm device. The alarm device may wake the subject or issue an alarm in response to the alarm signal, which may avoid health problems caused by a long-time apnea.

To avoid disturbances to a user by an alarm issued in case of a short-time apnea, in some embodiments, the alarm signal is not issued immediately once apnea of the subject is detected in a current state, but instead it is not issued to wake the subject until the duration of the apnea exceeds a preset duration threshold, e.g., 100 seconds. This improves the accuracy of the alarm and avoids undesired disturbances to the subject.

In some embodiments, when it is determined that the subject is experiencing an apnea and the duration of the apnea exceeds the preset duration threshold, the alarm signal may be sent to the alarm device (e.g., a terminal device or other appliances associated with the subject) via wireless network techniques to wake the subject or issue the alarm. The wireless network techniques may be short-distance wireless communication techniques such as Blue Tooth, wifi and so on. When the alarm device receives the alarm signal, it may wake the subject or report an emergency of the subject by means of vibration or sound prompts in accordance with the alarm signal.

In some embodiments, the alarm signal is sent wirelessly, which can avoid a trouble of wiring and hence is more convenient.

As a further possible implementation, the subject may be woken through an appliance being used by the subject, such as a pillow. For example, when the controller issues the alarm signal, the pillow may receive via a wireless network the alarm signal carrying a vibration instruction from the controller, and cause a vibrator contained therein to vibrate in response to the vibration instruction in the alarm signal, thereby waking the subject. The vibration instruction may comprise a control parameter(s) related to a vibration mode. The vibration parameter(s) may comprise information about vibration duration, vibration frequency and/or decibel during the vibration. For example, when the control parameters define the vibration duration to be 5 seconds and the vibration decibel to be 30 decibels, the vibrator can vibrate 5 seconds and produce a sound of 30 decibels during the vibration in response to the vibration instruction.

In some embodiments, by sending via the wireless network module the alarm signal to the vibrator in an appliance (e.g., a pillow) in direct contact with the subject, the subject can be rapidly woken, which avoids serious consequences caused by an excessively long-time apnea.

It can be understood that the apparatus for monitoring respiratory state may also be wired to the alarm device such that the apparatus for monitoring respiratory state sends the alarm signal to the alarm device in a wired manner.

Additionally, in some embodiments, prior to issuing the alarm signal, the method may further comprise: controlling a charge generator to switch on when it is determined that the user is experiencing an apnea. The charge generator generates charges in an ON state. The charges generated by the charge generator are collected by a charge collector. Only if an amount of the collected charges reaches a preset charge amount, the wireless network module is triggered to initiate so that the wireless network module sends the alarm signal, which improves the accuracy of sending the alarm signal.

In some embodiments, the airflow sensor may be filled with a material capable of adsorbing carbon dioxide (i.e., a carbon dioxide adsorbent). The carbon dioxide in the exhalation flow is adsorbed by the material. The state of the charge generator can be controlled based on a weight of the material with adsorbed carbon dioxide. Exemplarily, the charge generator 141 may be controlled to remain in an OFF state in response to the weight of the material with adsorbed carbon dioxide exceeding a preset weight threshold.

When the subject breathes normally, the carbon dioxide in the exhalation flow is adsorbed by the carbon dioxide adsorbent with which the airflow sensor is filled. Each time the subject breathes, the carbon dioxide in the exhalation flow will be adsorbed by the carbon dioxide adsorbent with which the airflow sensor is filled. By obtaining the weight of the material with adsorbed carbon dioxide and comparing the obtained weight with a preset weight threshold, it can be determined whether the subject is experiencing an apnea. For example, if the weight exceeds the preset weight threshold, it means that the subject is continuously exhaling carbon dioxide, and in this case, the charge generator can be controlled to remain in the OFF state. When the charge generator is in the OFF state, it does not generate charges. At this point, the charge collector collects no charges, i.e., the amount of collected charges stops increasing. Since the amount of the collected charges does not reach the preset charge amount, the wireless network module will not be initiated, so no alarm signal will be sent.

Correspondingly, when the subject is experiencing an apnea, no airflow is exhaled, so the weight of the carbon dioxide adsorbent in the airflow sensor does not change, and then the charge generator can be controlled to switch on. Alternatively, when the breathing of the subject is very weak, the exhalation flow is very small, so the weight of the material with adsorbed carbon dioxide is smaller than the weight threshold, and then the charge generator may be controlled to switch on. The charge generator generates charges in the ON state and the generated charges are collected by the charge collector. When the amount of the charges collected by the charge collector reaches the preset charge amount, the wireless network module is triggered to initiate such that the wireless network module transmits outward a signal in order to send the alarm signal.

In some application scenes, when the subject breathes, the carbon dioxide adsorbent with which the airflow sensor is filled will continuously adsorb carbon dioxide such that the carbon dioxide adsorbed by the material is accumulated. A possible result is that although the subject has experienced an apnea, no alarm signal will be sent since the charge generator is still in the OFF state due to the weight of the accumulated carbon dioxide exceeding the weight threshold.

To improve the accuracy of the alarm, in some embodiments, the material with adsorbed carbon dioxide is heated every time there is an airflow exhaled. The material with adsorbed carbon dioxide can release the adsorbed carbon dioxide when heated, such that the weight of the material can correctly reflect the exhalation flow, and that the sending of the alarm signal can be controlled accurately. Exemplarily, each time the airflow sensor detects an exhalation flow, i.e., each time the subject breathes, the heater can be switched on once for heating the airflow sensor such that the material with adsorbed carbon dioxide releases the adsorbed carbon dioxide, thereby restoring the material to an initial state in which it has not adsorbed carbon dioxide.

According to the embodiments of this disclosure, the carbon dioxide is released from the material with adsorbed carbon dioxide by heating, which not only recycles the material, but also avoids a problem that an alarm signal is not sent in case of an apnea of the subject, which is caused by a situation where the charge generator still remains in the OFF state due to accumulation of carbon dioxide in the airflows exhaled previously. As a result, the issuing of the alarm signal is more accurate.

In the method for monitoring respiratory state according to the embodiments of this disclosure, it is determined whether the subject is experiencing an apnea based on the monitored exhalation flow of the subject, and when the apnea occurs and the duration of the apnea exceeds a threshold, the alarm signal is issued to wake the user. This allows avoiding health problems caused by a long-time apnea.

Figure 7:
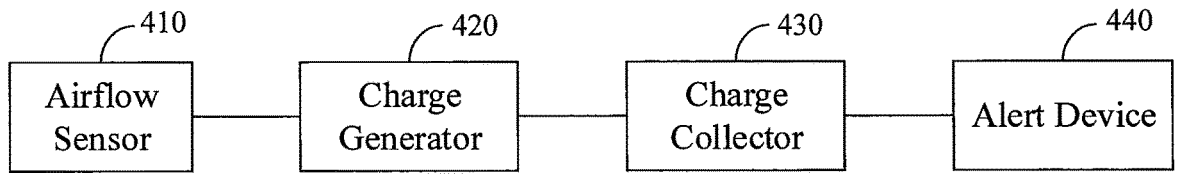
FIG. 7 is a schematic structure view of a still further apparatus for monitoring respiratory state provided in the embodiments of this disclosure.

FIG. 7 is a schematic structure view of a still further apparatus for monitoring respiratory state provided in the embodiments of this disclosure. As shown in FIG. 7, the apparatus for monitoring respiratory state comprises: an airflow sensor 410, a charge generator 420, a charge collector 430 and an alert device 440.

The airflow sensor 410 is configured to monitor an exhalation flow of a subject. In some embodiments, the airflow sensor 410 may be disposed above the human face or worn on the face of a subject in order to collect the exhalation flow of the subject. In order to avoid influences on the person's breathing and sleeping by the airflow sensor, a distance between the airflow sensor 410 and the face of the subject can be arranged within a preset distance threshold.

The charge generator 420 is coupled to the airflow sensor 410 and generates charges in an ON state. The charge generator 420 is configured to be in an OFF state when the subject breathes normally and in an ON state when the subject pauses breathing.

The charge collector 430 is connected with the charge generator 420 and configured to collect the charges generated by the charge generator when the charge generator 420 is in the ON state.

The alert device 440 is connected with the charge collector 430 and configured to issue an alarm signal when an amount of the charges collected by the charge collector 430 reaches a preset charge amount.

In some embodiments, the airflow sensor 410 monitors the airflow exhaled by the subject. Exemplarily, the airflow sensor 410 may comprise a gas sensitive material, which can change its electrical properties (e.g., resistance) depending on the exhalation flow of the subject, such that the airflow sensor 410 can output a corresponding airflow sensing signal (e.g., characterized by an electromotive force). When the airflow sensing signal indicates that the subject breathes normally, the charge generator 420 is in the OFF state and generates no charges. During this period of time, the charge collector 430 collects no charges. Since the charge amount is smaller than the preset charge amount, the alert device 440 will not issue the alarm signal. When the airflow sensing signal indicates that the subject pauses breathing, the charge generator 420 is in the ON state and continuously generates charges. During this period of time, the charge collector 430 collects the charges generated by the charge generator 420. The alert device 440 issues the alarm signal when an amount of the charges collected by the charge collector 430 reaches the preset charge amount. The alarm signal can be used for waking the subject or reporting an emergency of the subject, avoiding health problems caused by a long-time apnea.

The apparatus for monitoring respiratory state according to the embodiments of this disclosure can send out an alert based only on the exhalation flow of the subject and allows achieving the goal of monitoring respiratory state and sending out the alert with pure hardware, so it can be easily implemented.

In some embodiments, the alert device 440 itself may issue the alarm signal haptically (e.g., generating vibration) or acoustically (e.g., playing sounds). In other embodiments, when the amount of charges collected by the charge collector 430 reaches a preset charge amount, the alert device 440 may send the alarm signal to the alarm device (e.g., a terminal device), thereby waking the subject or issuing an alarm. The terminal device may be a mobile terminal such as a cellphone or a tablet computer, or a wearable device such as a smart wristband or a smart watch. Additionally or alternatively, the terminal device may also be a personal computer device.

In some embodiments, the alarm device may be a vibrator installed in a pillow of the subject. When the amount of charges collected by the charge collector 430 reaches the preset charge amount, the alert device 440 sends the alarm signal carrying a vibration instruction to the vibrator in the pillow of the subject, such that the vibrator vibrates according to the vibration instruction in the alarm signal, thereby waking the subject. Exemplarily, the vibration instruction may comprise information about vibration duration, decibel during the vibration and so on. For instance, in the vibration instruction, the vibration duration is 5 seconds and the vibration decibel is 30 decibels.

In some embodiments, the alert device may send the alarm signal to the vibrator in the pillow of the subject via a wireless network module, thereby waking the subject rapidly and avoiding serious consequences caused by an excessively long-time apnea.

In these embodiments, the charge generator 420 is controlled to switch on and off depending on the respiratory state of the subject. As a possible implementation, the airflow sensor 410 may comprise a gas sensitive resistor sensitive to carbon dioxide. The resistance of the gas sensitive resistor is decreased under the influence of carbon dioxide. The airflow sensor 410 can control the charge generator 420 to switch on and off by detecting an input voltage of the gas sensitive resistor. Exemplarily, the airflow sensor 410 detects the input voltage of the gas sensitive resistor, controls the charge generator in the OFF state if the input voltage exceeds a preset voltage value, and controls the charge generator in the ON state if the input voltage does not exceed the preset voltage value.

The apparatus for monitoring respiratory state according to the embodiments of this disclosure controls a charge generator to switch on or off based on the respiratory state of a subject, uses a charge collector to collect the charges generated when the charge generator is switched on, and issues an alarm signal by an alert device when the amount of accumulated charges reaches a preset charge amount, thereby avoiding health problems caused by a long-time apnea. The apparatus can send out an alert based only on the respiratory state of the subject without determining whether the subject is experiencing an apnea, and thus achieve the goal of monitoring respiratory state and sending out the alert merely with hardware, so it can be easily implemented.

Figure 8:
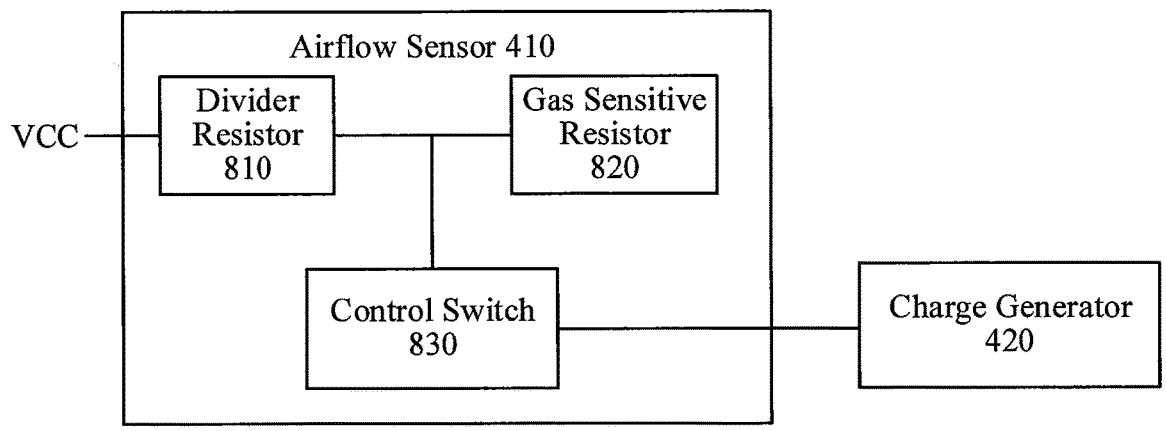
FIG. 8 is a circuit diagram of an airflow sensor provided in the embodiments of this disclosure.

FIG. 8 is a circuit diagram of an airflow sensor provided in the embodiments of this disclosure. As shown in FIG. 8, the airflow sensor 410 comprises a divider resistor 810, a gas sensitive resistor 820 and a control switch 830. A power source VCC is connected with one end of the divider resistor 810. The other end of the divider resistor 810 is connected with the gas sensitive resistor 820 and the control switch 830. The gas sensitive resistor 820 is also connected with the control switch 830.

When the subject breathes normally, the resistance value of the gas sensitive resistor 820 is decreased from an initial value under the influence of carbon dioxide, and the voltage across the divider resistor 810 rises. At this point, the airflow sensor detects an increase in the input voltage of the gas sensitive resistor 820. When the input voltage exceeds a preset voltage value, the control switch 830 controls the charge generator in an OFF state.

When the subject is experiencing an apnea, the airflow sensor monitors no exhalation flow, and then the resistance value of the gas sensitive resistor 820 is restored to the initial value, i.e., the maximum value. At his point, the voltage across the divider resistor 810 drops and the input voltage of the gas sensitive resistor 820 detected by the airflow sensor does not exceed the preset voltage value, so the control switch 830 controls the charge generator in an ON state.

For example, the preset voltage value is set to be 0.7V. When the subject breathes normally, the airflow sensor detects an increase in the input voltage of the gas sensitive resistor 820, and when the input voltage is greater than 0.7V, the charge generator is controlled to switch off. When the subject pauses breathing and the input voltage of the gas sensitive resistor 820 does not exceed 0.7V, the charge generator is controlled to switch on. The control switch may be implemented by a switch diode for example.

In some embodiments, the airflow sensor 410 is connected with a first switch on the charge generator 420. The first switch switches off the charge generator 420 when the input voltage of the gas sensitive resistor 820 exceeds the preset voltage value such that the charge generator 420 generators no charges. In other words, when the subject breathes normally, the first switch switches off the charge generator 420 such that the charge generator generates no charges. In some embodiments, the first switch may be implemented by a transistor.

Figure 9:
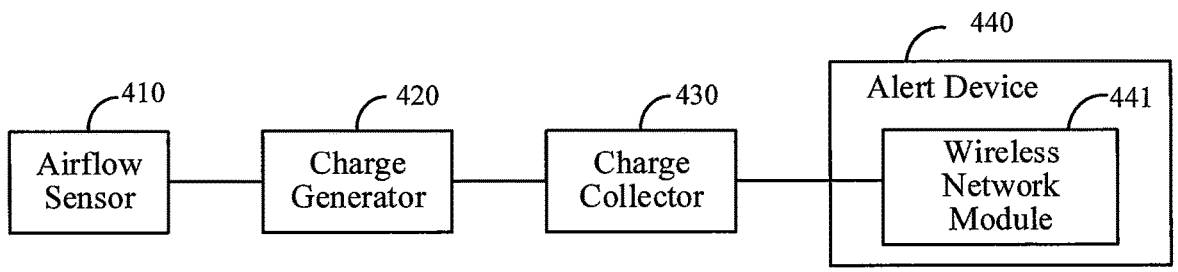
FIG. 9 is a schematic structure view of a still further apparatus for monitoring respiratory state provided in the embodiments of this disclosure.

FIG. 9 is a schematic structure view of a further apparatus for monitoring respiratory state provided in the embodiments of this disclosure. In addition to the airflow sensor 410, the charge generator 420, the charge collector 430 and an alert device 440 similar to those in FIG. 7, the alert device 440 shown in FIG. 9 further comprises a wireless network module 441 connected with the charge collector 430.

In some embodiments, the wireless network module 441 may be a short-distance wireless communication module like a Blue Tooth module, a wifi module and so on.

Exemplarily, the wireless network module 441 may be connected with the charge collector 430 via a second switch. When an amount of charges collected by the charge collector reaches a preset charge amount, the second switch is closed to trigger the wireless network module 441. The wireless network module 441 is triggered by the charges collected by the charge collector 430, thereby sending outward an alarm signal. An alarm device may wake the subject for example in response to the alarm signal.

In other words, when the second switch is closed, the charges collected by the charge collector may trigger the wireless network module to send outward the alarm signal. When the second switch is open, it means that the amount of charges collected by the charge collector is not sufficient for triggering the wireless network module to send outward the alarm signal.

In some embodiments, with the charge collector implemented in hardware, the wireless network module is triggered to send an alarm signal when the amount of the collected charges reaches a preset charge amount, which improves the accuracy of the alarm and avoids disturbances to the user caused by frequent sending of alarm signals.

Figure 10:
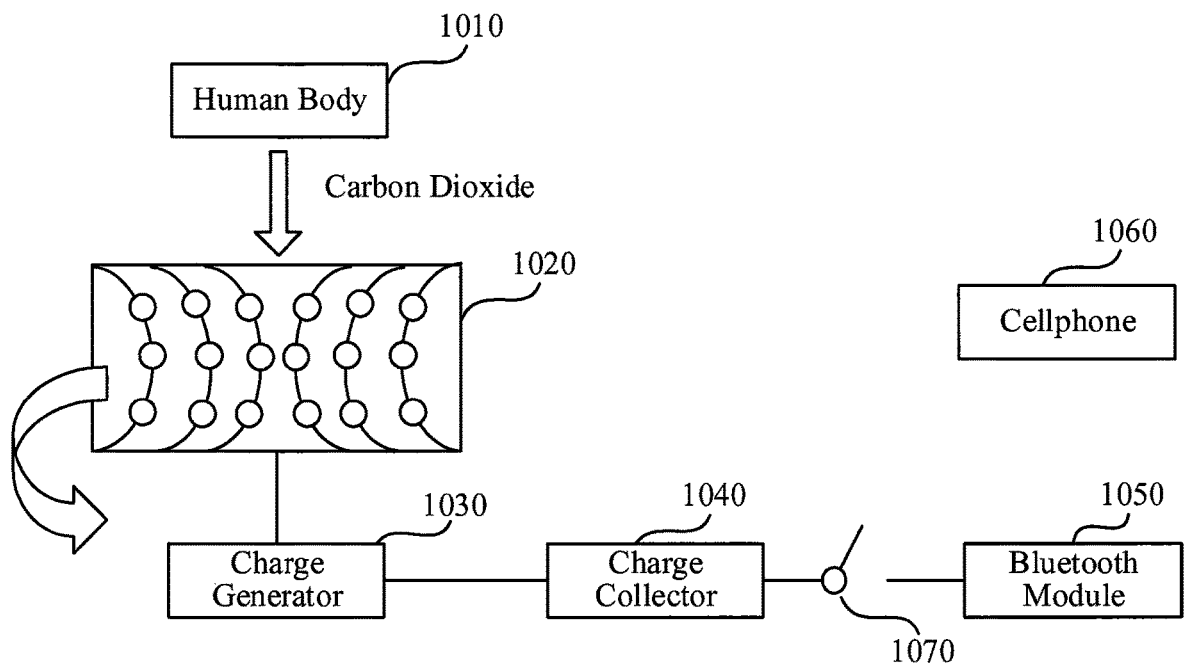
FIG. 10 is a schematic view showing a process of monitoring respiratory state provided in the embodiments of this disclosure.

In order to describe the above embodiments clearer, the apparatus for monitoring respiratory state provided in the above embodiments will be illustrated with reference to FIGS. 10 and 11. FIG. 10 is a schematic view showing a process of monitoring respiratory state provided in the embodiments of this disclosure. To take the sleep state as an example, as shown in FIG. 10, after the human body 1010 exhales carbon dioxide, carbon dioxide enters the airflow sensor 1020. The resistance of the gas sensitive resistor in the airflow sensor 1020 is changed, e.g., decreased, under the influence of carbon dioxide, such that the input voltage of the gas sensitive resistor exceeds a preset voltage value, thereby controlling the charge generator 1030 in an OFF state. Since the charge generator 1030 is in the OFF state, no charges are generated. The charge collector 1040 collects no charges. Accordingly, the switch 1070 between the charge collector 1040 and the Blue Tooth module 1050 is open, so the Blue Tooth module is not initiated. The Blue Tooth module 1050 will not send the alarm signal to the cellphone 1060.

Figure 11:
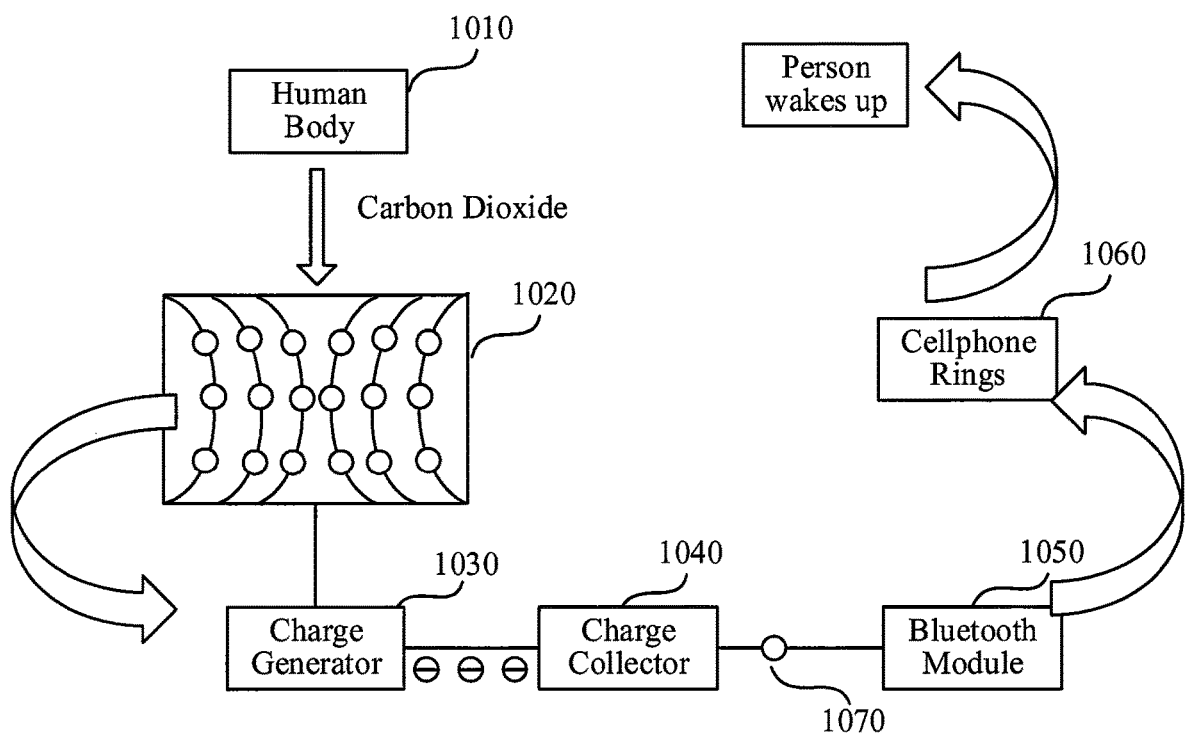
FIG. 11 is a schematic view showing a further process of monitoring respiratory state provided in the embodiments of this disclosure.

FIG. 11 is a schematic view showing another process of monitoring respiratory state provided in the embodiments of this disclosure. As shown in FIG. 11, when the human body 1010 pauses breathing, since no carbon dioxide is exhaled, no carbon dioxide will enter the airflow sensor 1020. At this point, the resistance value of the gas sensitive resistor is the initial value, i.e., the maximum value. The input voltage of the gas sensitive resistor drops as compared with when the human body is in a normal breathing state. When the input voltage is smaller than or equal to a preset voltage threshold, the charge generator 1030 is controlled to be in an ON state. The charge generator 1030 generates charges when in the ON state. The charge collector 1040 continuously collects charges. When the amount of charges collected by the charge collector is greater than a preset charge amount, the switch 1070 between the charge collector 1040 and the Blue Tooth module 1050 is closed to trigger initiation of the Blue Tooth module so that the Blue Tooth module sends an alarm signal to the cellphone 1060 via wireless signals. Upon receipt of the alarm signal, the cellphone 1060 rings to wake the person.

In the embodiments of this disclosure, a storage medium having computer instructions stored thereon is further provided, wherein the computer instructions when executed by a processor implement one or more steps of the method for monitoring respiratory state according to the embodiments of this disclosure.

In the embodiments of this disclosure, an electronic device is further provided, comprising one or more processors, the one or more processors being configured to execute computer instructions to implement one or more steps of the method for monitoring respiratory state according to the embodiments of this disclosure.

In the embodiments of this disclosure, a system for monitoring respiratory state is further provided, comprising: the apparatus for monitoring respiratory state according to the embodiments of this disclosure and an alarm device. The alarm device receives the alarm signal issued by the apparatus and acts in response to the alarm signal to wake the subject. In some embodiments, the alarm device comprises a terminal device configured to output an alarm signal in audible manner (e.g., music or voice) in order to wake the subject or issue an alarm. In other embodiments, the alarm device comprises an appliance on which the subject is lying, including a bed, a quilt or a pillow, and the appliance is used for vibrating in response to the alarm signal in order to wake the subject.

In the depictions of this description, terms such as "first" and "second" are used only for descriptive purposes and should not be construed as indicating or implying relative importance or hinting at the number of the indicated technical features. Thereby, a feature defined by "first" and "second" can comprise at least one feature explicitly or implicitly. In the depictions of this disclosure, "a plurality" means at least two, e.g., two, three and so on, unless prescribed otherwise explicitly and specifically.

Any process or method description described in the flowcharts or described otherwise herein can be understood to represent a module, segment or portion of codes comprising one or more executable instructions for implementing the steps of a customized logic function or process, and the scope of the preferred embodiments of this disclosure includes further implementations, in which the functions may not be performed in the order shown or discussed, including in a substantially simultaneous manner or in an inverse order depending on the functions involved. This should be understood by those skilled in the art to which the embodiments of the present disclosure pertain.

Logic and/or steps represented in the flowchart or described otherwise herein, for example, may be considered as an ordered list of executable instructions for implementing logical functions, and may be embodied in any computer readable medium, for use in an instruction execution system, apparatus, or device (e.g., a computer-based system, a system including a processor, or other systems that can fetch instructions from an instruction execution system, apparatus, or device and execute the instructions), or for use in combination with the instruction execution system, apparatus, or device. For this description, a "non-transitory computer readable medium" can be any device that can comprise, store, communicate, propagate, or transport programs for use in an instruction execution system, apparatus, or device, or for use in combination with the instruction execution system, apparatus, or device. More specific examples (a non-exhaustive list) of the computer readable medium include: an electrical connection (an electronic device) having one or more wires, a portable computer disk cartridge (a magnetic device), a random access memory (RAM), a read only memory (ROM), an erasable editable read only memory (EPROM or flash memory), a fiber optic device, and a portable compact disk read only memory (CDROM). In addition, the computer readable medium may even be paper or other suitable medium on which the programs can be printed since the programs can be obtained electronically (for example by optical scanning of the paper or other medium, followed by editing, interpretation or processing in other suitable manners if necessary), and then stored in a computer memory.

It should be understood that each part of this disclosure may be implemented by hardware, software, firmware or a combination thereof. In the above implementations, multiple steps or methods may be implemented by software or firmware stored in a memory and executed by a suitable instruction execution system. For example, if implemented in hardware, they can be implemented by any one or combination of the following techniques well known in the art: a discrete logical circuit with logic gates for implementing logic functions on data signals, an application specific integrated circuit with suitable combinational logic gates, a programmable gate array (PGA), a field programmable gate array (FPGA), and the like.

One having ordinary skills in the art can understand that all or part of the steps carried by the method for implementing the above embodiments can be completed by related hardware instructed by programs, and the programs can be stored in a computer readable storage medium and comprise one of the steps of the method embodiments or a combination thereof when executed.

In addition, the functional units in each embodiment of this disclosure may be integrated into one processing module, or each unit may exist physically and independently, or two or more units may be integrated into one module. The integrated module may be implemented either in the form of hardware or in the form of a software functional module. The integrated module may also be stored in a computer readable storage medium if it is implemented in the form of a software functional module and sold or used as an independent product.

The storage medium mentioned above may be a read only memory, a magnetic disk or an optic disk, etc. Although the embodiments of this disclosure have been shown and described, it can be understood that the embodiments are exemplary, and they cannot be construed as limiting this disclosure, and one having ordinary skills in the art can vary, change, substitute and modify the above embodiments within the scope of this disclosure.

The invention claimed is:

1. An apparatus for monitoring respiratory state, comprising:
an airflow sensor configured to monitor an exhalation flow of a subject;
a controller configured to determine whether the subject is experiencing an apnea according to monitored exhalation flow and issue an alarm signal in response to determining that the subject is experiencing the apnea;
a wireless network module, wherein the controller is further configured to issue the alarm signal by sending the alarm signal to an alarm device via the wireless network module; and
a trigger connected with the controller and the wireless network module respectively and configured to trigger initiation of the wireless network module, and comprising:
a charge generator coupled to the controller, and configured to be controlled to switch on in response to the controller determining that the subject is experiencing the apnea, and generate charges in an ON state, and
a charge collector connected with the charge generator and the wireless network module respectively, and configured to collect the charges generated by the charge generator, and trigger initiation of the wireless network module in response to an amount of the collected charges reaching a preset charge amount such that the wireless network module sends the alarm signal by transmitting outward the alarm signal;
wherein the airflow sensor is filled with a material configured to adsorb carbon dioxide, wherein the carbon dioxide in the exhalation flow is adsorbed by the material, and
wherein the controller is further configured to obtain a weight of the material with adsorbed carbon dioxide and control the charge generator to be in an OFF state in response to an obtained weight exceeding a preset weight threshold.

2. The apparatus according to claim 1, wherein the airflow sensor comprises an air flow amount sensor, and wherein the controller is configured to:
compare an air flow amount of the exhalation flow monitored by the air flow amount sensor with a preset flow mount threshold;
determine that the subject is experiencing the apnea in response to the air flow amount of the exhalation flow being lower than the preset flow mount threshold; and
issue the alarm signal in response to determining that the subject is experiencing the apnea and a duration of the apnea exceeding a preset duration threshold.

3. The apparatus according to claim 1,
wherein the alarm device comprises a terminal device associated with the subject, and
wherein the terminal device wakes the subject or reports an emergency of the subject haptically or audibly.

4. The apparatus according to claim 1,
wherein the alarm device comprises a vibrator in an appliance in contact with the subject, and
wherein the alarm signal carries a vibration instruction such that the vibrator vibrates in accordance with the vibration instruction to wake the subject.

5. The apparatus according to claim 1, further comprising:
a heater,
wherein the controller is further configured to control the heater to switch on upon detection of the exhalation flow by the airflow sensor so as to heat the material with the adsorbed carbon dioxide to release the adsorbed carbon dioxide.

6. A method for monitoring respiratory state, comprising:
monitoring an exhalation flow of a subject;
determining whether the subject is experiencing an apnea according to a monitored exhalation flow; and
issuing an alarm signal in response to determining that the subject is experiencing the apnea;
wherein said issuing the alarm signal further comprises:
controlling a charge generator to switch on to generate charges in response to determining that the subject is experiencing the apnea;

collecting, by a charge collector, the charges generated by the charge generator; and triggering to send the alarm signal wirelessly in response to an amount of the charges collected by the charge collector reaching a preset charge amount;

wherein the method further comprises:
adsorbing carbon dioxide in the exhalation flow with a material capable of adsorbing carbon dioxide;

obtaining a weight of the material with adsorbed carbon dioxide;

comparing an obtained weight with a preset weight threshold; and controlling the charge generator to be in an OFF state in response to the weight exceeding the preset weight threshold.

7. The method according to claim 6, wherein determining whether the subject is experiencing the apnea comprises:
comparing an air flow amount of the monitored exhalation flow with a preset flow mount threshold; and determining that the subject is experiencing the apnea in response to the air flow amount of the exhalation flow being lower than the preset flow mount threshold, wherein the alarm signal is issued in response to determining that the subject is experiencing the apnea and determining that a duration of the apnea exceeding a preset duration threshold.

8. The method according to claim 6, wherein issuing the alarm signal comprises:
sending the alarm signal to an alarm device wirelessly.

9. The method according to claim 6,
wherein the alarm signal is sent to an alarm device that comprises a terminal device associated with the subject, and wherein the alarm device wakes the subject or reports an emergency of the subject haptically or audibly.

10. The method according to claim 6, further comprising:
upon detection of the exhalation flow, heating the material with the adsorbed carbon dioxide to release the adsorbed carbon dioxide.

11. An apparatus for monitoring respiratory state, comprising:
an airflow sensor configured to monitor an exhalation flow of a subject; and a controller configured to determine whether the subject is experiencing an apnea according to monitored exhalation flow and issue an alarm signal in response to determining that the subject is experiencing the apnea, wherein the controller comprises:
a charge generator coupled to the airflow sensor, and configured to be in an OFF state in response to the monitored exhalation flow indicating that the subject breathes normally and in an ON state in response to the monitored exhalation flow indicating that the subject pauses breathing, wherein the charge generator generates charges in the ON state, and a charge collector connected with the charge generator and configured to collect the charges generated by the charge generator when the charge generator is in the ON state;

wherein the controller is configured to determine that the subject is experiencing the apnea in response to an amount of the charges collected by the charge collector reaching a preset charge amount, wherein the apparatus further comprises an alert device connected with the charge collector and configured to issue the alarm signal in response to the amount of the charges collected by the charge collector reaching the preset charge amount, wherein the airflow sensor comprises a gas sensitive resistor sensitive to carbon dioxide, and wherein the airflow sensor is configured to detect an input voltage of the gas sensitive resistor, control the charge generator to be in the ON state when the input voltage does not exceed a preset voltage value, and control the charge generator to be in the OFF state when the input voltage exceeds the preset voltage value.

12. The apparatus according to claim 11,
wherein the airflow sensor is connected with the charge generator via a first switch, and wherein the first switch switches off the charge generator in response to the input voltage exceeding the preset voltage value.

13. The apparatus according to claim 11,
wherein the alert device further comprises a wireless network module connected with the charge collector, wherein the wireless network module is connected with the charge collector via a second switch, wherein the second switch is closed in response to the amount of the charges collected by the charge collector reaching the preset charge amount, and wherein the wireless network module is configured to send outward the alarm signal in response to the second switch being closed.

14. A system for monitoring a respiratory state, comprising:
the apparatus for monitoring the respiratory state according to claim 1; and an alarm device configured to receive the alarm signal issued by the apparatus and wake the subject or report an emergency of the subject in response to the alarm signal.

15. A system for monitoring a respiratory state, comprising:
the apparatus for monitoring the respiratory state according to claim 11; and an alarm device configured to receive the alarm signal issued by the apparatus and wake the subject or report an emergency of the subject in response to the alarm signal.

* * * * *